United States Patent [19]

Thomson

[11] Patent Number: 4,816,440

[45] Date of Patent: Mar. 28, 1989

[54] STABLE FORMULATION OF BIOLOGICALLY ACTIVE PROTEINS FOR PARENTERAL INJECTION

[75] Inventor: James W. Thomson, Albany, Calif.

[73] Assignee: Cetus Corporation, Emeryville, Calif.

[21] Appl. No.: 780,551

[22] Filed: Sep. 26, 1985

[51] Int. Cl.$^4$ ...................... A61K 37/02; A61K 45/02
[52] U.S. Cl. ........................................ 514/12; 424/85.6
[58] Field of Search ............................ 424/85; 435/68; 530/351; 514/12

[56] References Cited

U.S. PATENT DOCUMENTS 3,658,970  4/1972  Carroll .
3,667,929  6/1972  Fleming, Jr. .
4,331,653  5/1982  Brown et al. .
4,450,103  5/1984  Konrad et al. .
4,462,940  7/1984  Hanisch et al. .
4,604,377  8/1986  Fernandes et al. .................... 435/68

FOREIGN PATENT DOCUMENTS 1113926  12/1981  Canada .
81104812  8/1981  Japan .
8280314  5/1982  Japan .
8288126  6/1982  Japan .

OTHER PUBLICATIONS

Wang et al., *J. Parenteral Drug Assoc.*, 34, 452–462 (1980).

*Primary Examiner*—Blondel Hazel
*Attorney, Agent, or Firm*—Janet E. Hasak; Philip L. McGarrigle

[57] ABSTRACT

A pharmaceutical composition containing IL-2 or IFN-$\beta$ dissolved in a suitable carrier medium at pH 7.0 to 8.0 stabilized with sodium laurate is suitable for parenteral injection into humans or animals. This formulation may be prepared by adding to either protein, after its recovery from a transformed organism, an effective amount of sodium laurate at a pH of 9 to 9.5 and then adjusting the pH of the formulation to between 7.0 and 8.0.

10 Claims, 2 Drawing Sheets

STABLE FORMULATION OF BIOLOGICALLY ACTIVE PROTEINS FOR PARENTERAL INJECTION

BACKGROUND OF THE INVENTION

1. Field of the Invention

This invention is in the field of biochemical engineering. More particularly, the invention concerns a pharmaceutical formulation of biologically active recombinant IL-2 or IFN-$\beta$ protein which is suitable for parenteral injection into humans.

2. Description of Related Disclosures

Naturally occurring interferons (IFNs) are species-specific proteins, often glycoproteins, produced by various cells upon induction with viruses double stranded RNA's, other polynucleotides, antigens and mitogens. Interferons exhibit multiple biological activities such as antiviral, antiproliferative, immunomodulatory and anticellular functions. At least three distinct types of human interferons have been identified and characterized in terms of their anti-viral, anti-growth and activation of natural killer cell (NK) activities. They are produced by leukocytes, lymphocytes, fibroblasts and the immune system and are classified as $\alpha$, $\beta$ and $\gamma$ interferons. These are reported to be different proteins coded for by distinct structural genes.

In recent times, however, several of the human interferon genes have been cloned using recombinant DNA technology and expressed in *E. coli* (Nagola, S. et al., *Nature*, 284:316 (1980); Goeddel, D. V. et al., *Nature*, 287–411 (1980); Yelverton, E. et al., *Nuc Acid Res*, 9:731 (1981)); and Streuli, M. et al., *Proc Natl Acad Sci (US)*, 78:2848 (1981).

Native human IL-2 is an antigen-nonspecific, genetically unrestricted soluble factor produced by erythrocyte rosette positive T cells stimulated with antigens, mitogens and alloantigens. It is a protein with a reported molecular weight in the approximate range of 13,000 to 17,000 daltons (S. Gillis and J. Watson, *J Exp Med* (1980) 159:1709) and an isoelectric point in the approximate range of pH 6–8.5. Human IL-2 has a number of in vitro and in vivo effects including enhancing the proliferative responses of human peripheral blood mononuclear cells or murine thymocytes, enhancing the immune response in humans and in animals against bacterial, parasitic, fungal, protozoan and viral infections, and supporting the growth of continuous T cell lines.

Proteins such as IFNs and IL-2 and muteins thereof in which a cysteine residue is deleted or replaced with another amino acid have been produced microbially through genetic engineering techniques. Microbially produced IL-2 is not glycosylated and is produced in a reduced state by the microorganisms. When purified and oxidized, these microbially produced IL-2s exhibit activity comparable to native human IL-2.

Procedures for purifying native IL-2 from T cells are described by Watson, J., et al, *J Exp Med* (1979) 150:849–861; Gillis, S., et al, *J Immunology* (1980) 124:1954–1962; Mochizuki, D. Y., et al, *J Immun Meth* (1980) 39:185–201; Welte, K., et al, *J Exp Med* (1982) 156:454–464; and European patent applications 83103582.9 (published Oct. 26, 1983 under no. 92163) and 83400938.3 (published Nov. 16, 1983 under no. 94317). In general, these procedures involve precipitating proteins from culture supernatants with ammonium sulfate followed by a chromatographic fractionation.

Procedures for recovering and purifying bacterially produced IFNs are described in U.S. Pat. Nos. 4,450,103; 4,315,852; 4,343,735; and 4,343,736; and Derynck, R., et al, *Nature* (1980) 287:193–197 and Scandella and Kornberg, *Biochemistry*, 10:4447 (1971). Generally with these methods the IFN is not produced in a sufficiently pure form and in sufficiently large quantities for clinical and therapeutic purposes and the resulting IFN preparations produced by recombinant DNA techniques have residual toxic amounts of chemicals, such as sodium dodecyl sulfate (SDS) and other surfactants or precipitants used in the extraction and purification steps which are not acceptable for clinical studies in therapeutic applications.

Both recombinant IFN-$\beta$ and IL-2 are insoluble in solutions which are at a physiological pH of 7 to 8. Therefore, various processes and additives have been devised to solubilize these proteins.

U.S. Pat. No. 4,463,940 to Hanisch et al. discloses a process for formulating interferon by mixing the interferon and normal serum albumin at pH 12.0 for 5 minutes and then adjusting the pH to 7.5 to obtain a soluble mixture. Exposing the interferon to such a high pH may adversely affect the properties of the interferon. In addition, the formulation contains some SDS.

The only alternatives to the high pH albumin formulation are the addition of detergents or of chaotropic agents such as urea or guanidine hydrochloride to the formulation to solubilize the protein. A detergent such as sodium dodecyl sulfate will cause hemolysis upon injection if its concentration is sufficiently high. Additionally, even a relatively low level of SDS where approximately one molecule of SDS is bound to each molecule of IL-2 may cause liver damage if the IL-2 formulation is administered at very high doses. Chaotropic agents such as urea work to solubilize IL-2, but must be used at very high concentrations of 30% or higher solutions. In addition, with urea there are problems with chemical modification of the protein at high concentrations.

A reagent-grade IL-2 which is in solution with the detergent N-lauryl sarcosinate has been commercialized. In addition, an IL-2 formulation is being sold which contains reagent-grade IL-2 and is recommended to be reconstituted in a complete tissue culture medium with 0.5% deoxycholate, another detergent. Such formulations, however, are not suitable for parenteral injection into humans.

Fatty acids have been used as pharmaceutical absorption promoters for oral and vaginal administration and for rectal application. See, e.g., Jap. Kokai Nos. 8288126 and 8280314 to Kyoto Pharmaceutical Industries. See also Canadian Pat. No. 1113926 and Jap. Kokai 81104812 to Sankyo Co., Ltd. In addition, fatty acids are known for use in topical creams (U.S. Pat. No. 4,331,653), in effecting dissolution of solutes in water (U.S. Pat. No. 3,667,929) and for pharmaceutical injection (U.S. Pat. No. 3,658,970-lauric acid).

Wang et al, *J. Parenteral Drug Assoc*, 34, 452–462 (1980) provides a review of excipients and pH's for parenteral products used in the United States. This article indicates that it is not trivial to choose excipients for parenteral products as for other dosage forms due to concerns for safety and feasibility in sterilization. Acceptance of a substance to be used as excipient often involves lengthy safety testing or production trials.

Also, for reasons of stability or solubility the pH of the product cannot always be adjusted to physiological pH of 7.4. A list of solubilizing agents such as detergents and lipids in use for various drugs is provided on p. 454 and a list of stablizers, including sodium caprylate (octanoate) for normal serum albumin, is provided on p. 458.

There is a need in the art for a protein formulation where the protein is not subjected to high alkalinity so as to alter the protein, the protein is soluble and the formulation is free or virtually free of SDS.

SUMMARY OF THE INVENTION

The present invention provides a stable pharmaceutical composition of matter suitable for parenteral injection into animals and humans comprising a therapeutically effective amount of recombinant interleukin-2 or $\beta$-interferon protein purified to contain less than 4 $\mu$g sodium dodecyl sulfate per mg protein and purified from other bacterial or cellular materials which protein is dissolved in an inert carrier medium comprising sodium laurate at a pH of between 7.0 and 8.0. In such a formulation the protein is in a soluble form at physiological pH and the pH need not be raised to above 10.5 to obtain such a soluble formulation. Moreover, sodium laurate naturally occurs in the blood. A compound similar to sodium laurate, sodium octanoate, which is a known stabilizer for human serum albumin, is not an effective stabilizer for the biologically active protein IL-2.

This composition is prepared by an improved process comprising (a) extracting the recombinant protein (IL-2 or IFN-$\beta$) from the disruptate of a host organism transformed to produce the protein, (b) purifying the protein to contain less than 4 $\mu$g sodium dodecyl sulfate per mg protein, (c) mixing the purified protein in an inert carrier medium with an effective amount of sodium laurate at a pH of about 9 to 9.5, (d) adjusting the pH of the formulation to between about 7.0 and 8.0, and preferably (e) lyophilizing the formulation.

In preferred embodiments of this invention the stabilizer is present in a concentration of 0.03 to 0.1% by weight, depending on the exact pH of the solution, the solubilizing agent used in the process is SDS, the formulation further comprises mannitol, and the pH thereof is 7.5 to 7.7.

DESCRIPTION OF THE PREFERRED EMBODIMENTS

Figure 1:
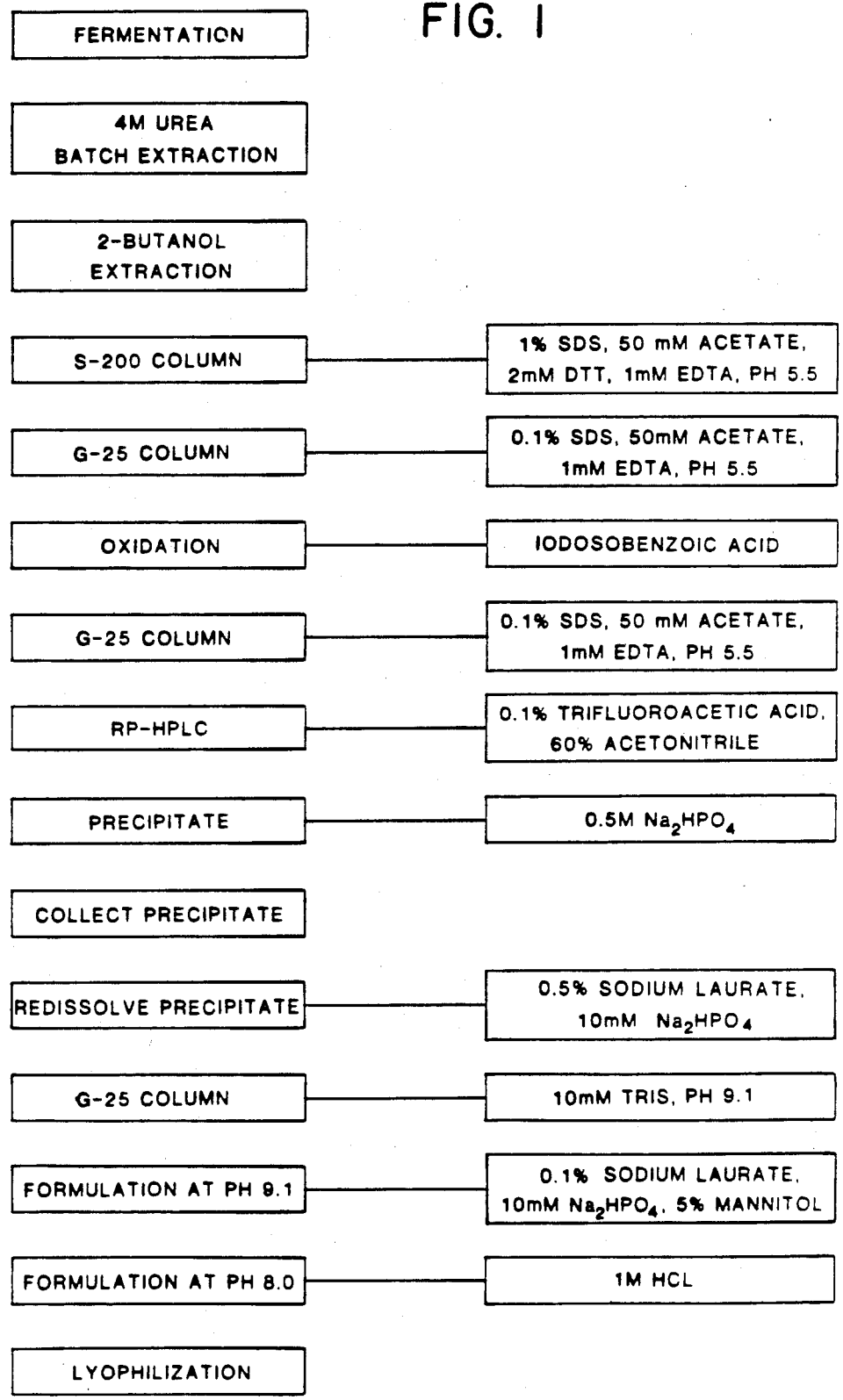
FIG. 1 shows a flow diagram of a preferred procedure for processing microbially produced IL-2 and formulating it at pH 8.0.

The term "recombinant" refers to IL-2 and IFN-$\beta$ proteins generated using genetic engineering techniques. These techniques typically involve identifying and characterizing the structural gene which encodes the native protein, isolating or synthesizing that gene or a mutant which encodes a functionally equivalent mutein of the native protein, inserting the gene into an appropriate expression vector in a position which permits expression of the gene, transforming competent hosts with the vector, identifying correct transformants, and culturing the transformants in a suitable growth medium. The host organism may be yeast or mammalian cells, but is preferably microorganisms, more preferably bacteria, and most preferably E. coli. The IL-2 and IFN-$\beta$ are typically recovered from the culture by disrupting the cells, treating the cellular debris with solubilizing agents (depending on the solubility characteristics of the protein) and one or more extractants to isolate the crude protein, and purifying the crude protein by various preparative chromatographic procedures. If the protein is susceptible to oligomer formation during the fermentation or recovery processes, the protein may be treated with a reducing agent at an appropriate stage in the recovery process.

As used herein, the term "$\beta$-HIFN" refers to human $\beta$-interferon or $\beta$-interferon-like polypeptides produced by recombinant DNA techniques, and whose amino acid sequence is the same, similar or substantially homologous to native $\beta$-interferon, both the glycosylated and the unglycosylated protein. Examples of such recombinant proteins are the IFNs described by Nagola, S., et al., Nature, 284:316 (1980), Goeddel, D. V., et al., Nature, 287:411 (1980), Yelverton, E., et al., Nuc Acid Res, 9:731 (1981), Streuli, M., et al., Proc Nat'l Acad Sci USA, 78:2848 (1981), European Patent Publication No. 28,033 published June 6, 1981 and European Patent Publication No. 109,748 published May 30, 1984.

As used herein the term "IL-2" denotes a protein which is native interleukin-2 or is produced by a host that has been transformed with a human interleukin-2 gene or a modification of the human interleukin-2 gene which encodes a protein having: (a) an amino acid sequence that is at least substantially identical to the amino acid sequence of native human interleukin-2 and (b) biological activity that is common to native human interleukin-2. Substantial identity of amino acid sequences means the sequences are identical or differ by one or more amino acid alterations (deletions, additions, substitutions) that do not cause an adverse functional dissimilarity between the synthetic protein and native human interleukin-2. Examples of such recombinant proteins are the IL-2s described in European patent application No. 83101035.0 filed Feb. 3, 1983 (published Oct. 19, 1983 under publication no. 91539), European patent application No. 82307036.2 filed Dec. 22, 1982 (published Sept. 14, 1983 under No. 88195), European patent application No. 83306221.9 filed Oct. 13, 1983 (published May 30, 1984 under no. 109748), and the IL-2s described in the examples of this application.

The IL-2 and $\beta$-HIFN particularly preferred herein are muteins of biologically active IL-2 and $\beta$-HIFN in which one or more cysteine residues which are not essential to biological activity have been deliberately deleted or replaced with other amino acids to eliminate sites for intermolecular crosslinking or incorrect intramolecular disulfide bond formation. More preferably the protein herein is a IFN-$\beta$ mutein, with the cysteine residue at amino acid position 17 of the native counterpart replaced by a serine residue (designated IFN-$\beta_{ser17}$) or an IL-2 mutein with the cysteine residue at amino acid position 125 of the native couanterpart replaced by a serine residue (designated IL-$2_{ser125}$), or with the initial alanine residue of the native counterpart eliminated, or with the initial alanine residue eliminated and the cysteine at position 125 replaced by serine (designated des-Ala-Ser$_{125}$IL-2).

The composition herein is formulated in a medium defined further below containing an effective amount of a particular type of stabilizer which is designed to dissolve the protein in the medium and which is non-toxic and therapeutically compatible.

The word "inert" in describing the medium refers to media which in the formulaton will not interfere with the biological activity of the IL-2 or β-HIFN protein contained in the formulation.

In general, the recovery, purification and formulation process herein involves fermenting the host organism transformed to express the protein, disrupting the cell membrane of the host organism, extracting the bacterial proteins from the disruptate using low concentrations of a chaotropic agent, recovering the protein using a solubilizing agent, extracting the protein with 2-butanol or 2-methyl-2-butanol, subjecting the extracted protein to chromatographic purification, precipitating the protein by neutralization, redissolving the precipitate in a chaotropic agent, removing the SDS, formulating the protein at pH 9 to 9.5 in the medium with the sodium laurate, adjusting the pH of the formulation to between 7.0 and 8.0, inclusive, and lyophilizing the formulation. The preferred embodiment of the process of this invention for formulating recombinant IL-2 produced from microorganism hosts is summarized below.

The transformed microorganisms may be grown in a suitable growth medium, typically to an optical density (OD) of at least about 30 at 680 nm, and preferably between about 20 and 40 at 680 nm. The composition of the growth medium will depend upon the particular microorganism involved. The medium is an aqueous medium containing compounds that fulfill the nutritional requirements of the microorganism. Growth media will typically contain assimilable sources of carbon and nitrogen, energy sources, magnesium, potassium and sodium ions, and optionally amino acids and purine and pyrimidine bases. (See *Review of Medical Biology*, Lange Medical Publications, 14th Ed pp 80–85 (1980).) In expression vectors involving the trp promoter, the tryptophan concentration in the medium is carefully controlled to become limiting at the time IL-2 expression is desired. Growth media for *E. coli* are well known in the art.

After the cells are harvested from the culture, they may be concentrated, if necessary, to about 20 to 150 mg/ml, preferably 80 to 100 mg/ml (OD 40 to 300, preferably 160 to 200 at 680 nm) by filtration, centrifugation, or other conventional methods.

Following concentration the cell membranes of the transformed microorganisms ma be disrupted. The main purpose of disruption is to facilitate the following extraction and solubilization steps. Conventional cell disruption techniques such as homogenization, sonication, or pressure cycling may be used in this step of the process. Preferred methods are sonication or homogenization with a Manton-Gaulin homogenizer. The end point of the disruption step may be monitored by optical density, with the optical density of the suspension typically decreasing about 65% to 85%. In any event, the disruption should break substantially all of the cells so that substantially no intact cells are carried through to the solubilization step. Before the disruption, the pH of the liquid phase of the concentrate is adjusted, if necessary, to a level that facilitates removal of *E. coli* proteins in subsequent steps, while retaining IL-2 protein as an insoluble complex in the cellular debris. The pH may be so adjusted by adding suitable buffers. In most instances pHs in the range of about 8 to about 8.5 will be used.

The steps in the recovery process subsequent to the disruption step are primarily designed to separate the IL-2 from *E. coli* proteins to a high level of purity (preferably at least about 95% and more preferably at least about 98%) in good yields while maintaining the IL-2 in a reduced state. Simultaneously, these purification processes, in combination, also reduce pyrogenic substances in the final product to a level believed to be acceptable for parenteral administration to patients.

After the cells have been disrupted the particulate matter may be separated from the liquid phase of the disruptate and resuspended in an aqueous medium buffered to the optimal pH for the extraction. The particulate matter may optionally be washed with buffer at this stage to remove any water-soluble *E. coli* proteins therein. In any event, the protein concentration of the cell suspension subjected to the extraction will usually be in the range of about 5 to about 60 mg/ml, preferably 20 to 40 mg/ml.

The extraction of *E. coli* proteins from the particulate cellular material may be carried out concurrently with the disruption or sequentially following the disruption. It is preferably carried out as a separate step following the disruption. The extractant is an aqueous solution of a chaotropic agent (i.e., a mild protein denaturant that dissociates hydrogen bonds and affects the tertiary structure of proteins). The extractant selectively removes the bulk of the *E. coli* proteins from the cellular debris leaving at least a substantial portion of the IL-2 associated (container in or bound to) with the cellular debris. The selectivity is facilitated by the hydrophobicity of the IL-2 and the fact that it is in a reduced, insoluble state at a pH near the isoelectric point of the protein. In addition, a substantial portion of the IL-2 may be present in vivo as inclusion bodies of significant mass, as has been the case with other cloned proteins expressed at high levels in *E. coli*. Examples of extractants include sodium laurate, urea, guanidinium hydrochloride (guanidinium hydrochloride should not be used when SDS is used as a solubilizing agent), and sodium thiocyanate. Urea is preferred. The concentration of the chaotropic agent in the extraction mixture will depend upon the particular agent that is used and the amount of cellular material in the extraction mixture. In the case of urea, concentrations (final) between about 3.5M and 4.5M, preferably about 4 M, will be used in batch processes at 25° C. If the extraction is run on a continuous basis over longer time periods it may be desirable to use lower concentrations. Temperatures in the range of 20° C. to 25° C. will normally be used in extraction, with room temperature being used for convenience. Mixing will typically be used to enhance contact between the solution and particulate matter and thus decrease the time required to extract non-IL-2 proteins from the cellular debris. Kinetic analysis of the extraction process was performed on the supernatants using SDS-PAGE, and the extraction was found to be essentially complete by 15–30 minutes.

Following the extraction, the mixture may be separated into solid and liquid phases. The IL-2 in the solid phase is then selectively solublized by contacting the solid phase with a neutral, aqueous buffer containing a reducing agent and a solubilizing agent. Surface active agents (detergents) that have a suitable hydrophobic-hydrophilic balance to solubilize the hydrophobic IL-2 may be used. Alkali metal sulfates containing 10 to 14 carbon atoms and alkali metal alkyl sarcosinates are preferred solubilizing agents, with SDS and sarcosyl being particularly preferred.

The amount of solubilizing agent used in the solubilization will depend upon the particular agent. When SDS or sarcosyl are used, the preferred ratio (w/w) of SDS/sarcosyl to solid phase protein is about 0.5:1 to 1.4:1. The solubilizing medium also contains a sufficient amount of reducing agent to prevent the solubilized IL-2 from undergoing oxidation to any significant degree. Protein reducing agents such as dithiothreitol (DTT) and 2-mercaptoethanol may be used. The concentration of reducing agent such as DTT in the medium will usually range between about 5 to 20 mM. The solubilization will typically be carried out at temperatures in the range of 20° C. to 25° C. with mixing to facilitate contact between the solid phase and the solubilizing medium. Higher temperatures may solubilize unwanted E. coli proteins. The solublization is considered complete when the sample has sat 15 minutes or the solution turns translucent. Insoluble material is separated after completing the solubilization.

After the IL-2 is solubilized the IL-2 may be extracted from the aqueous solution under reducing conditions with 2-butanol or 2-methyl-2-butanol to remove additional E. coli proteins, notably including certain contaminants that have molecular weights very close to the IL-2. Conditions (e.g., ionic strengths in the range of 0.05 and 0.15) at which the aqueous solution and butanol are substantially immiscible are used. In carrying out the organic extraction the protein concentration of the aqueous solution is preferably adjusted, if necessary, to less than about 6 mg/ml, preferably about 0.5 to 4 mg/ml. Reducing conditions are mainained by carrying out the extraction in the presence of a reducing agent (e.g., DTT). The butanol will normally be added to the aqueous solution of solubilized IL-2 in volume ratos in the range of about 1:1 to about 3:1 (extractant:aqueous solution), preferably about 1:1. The extraction may be carried out in a batch or continuous operation. The temperature will normally be in the range of 20° C. to 100° C. and the pH will normally be about 4 to 9, preferably about 5 to 6. The time of contact between the solution and the butanol is not critical and relatively short times on the order of a few minutes may be used. After the extraction is complete, the aqueous phase and butanol phase are separated and the IL-2 is separated from the butanol phase. A preferred procedure for separating the IL-2 from the butanol phase is acid precipitation. This is done by adding the butanol phase to aqueous buffer, pH 7.5 until the organic phase is dissolved (approximately 2-3 volume buffer per volume of organic), and then lowering the pH to about 5.5 to 7.0, preferably 6.0 to 6.2, to cause the IL-2 to precipitate.

In a subsequent step the IL-2 may be separated from any E. coli contaminants remaining after the extraction(s) and optimally from the solubilizing agent. Gel filtration chromatography, RP-HPLC, or a combination of gel filtration chromatography and RP-HPLC is used. The gel filtration chromatography is preferably carried out in two stages that remove both pyrogenic components and protein contaminants having molecular weights higher or lower than IL-2. (IL-2 has a molecular weight of about 15.5K daltons.) Gels that are capable of fractionating the solution to permit separation of the IL-2 from these contaminants are commercially available. Sephacryl S-200 is a preferred gel for removing the higher molecular weight components and Sephadex G-25, G-75 or G-100 gels are preferred for removing the low molecular weight contaminants. The gel filtrations will typically be run in buffered solutions (pH 5.5 to 7.0) containing about 0.1% to 1.0% solublizing agent and about 1 to 10 mM reducing agent. The column will be sized to permit suitable resolution of the desired components.

RP-HPLC is an alternative to gel filtration. Also, RP-HPLC is capable of removing molecules from the solution that have molecular weights close to IL-2 and cannot, therefore, be removed completely by gel filtration. In addition, contaminants such as bacterial endotoxin are also removed effectively by RP-HPLC. Therefore, RP-HPLC may also be used as a final purification step after gel filtration. Supports (stationary phases) that provide good resolution of proteins may be used in the RP-HPLC. C-4, C-8, or C-18 on 300 angstrom pore-size supports are examples of preferred supports. The separation is carried out at an acidic pH of less than about 2.3, usually 2.1 to 2.3, in order to keep the IL-2 in solution. In this regard, the pH of the solution from the solublization (gel filtration) will preferably be adjusted to this range. The solution is loaded into the RP-HPLC column and is adsorbed onto the stationary phase. A gradient solvent system comprising an organic acid such as acetic acid or trifluoroacetic acid and organic solvent such as propanol or acetonitrile may be used to elute the IL-2 from the column. Acetic acid-propanol, trifluoroacetic acid-propanol, and trifluoroacetic acid-acetonitrile are preferred solvent systems. IL-2 elutes in the acetic acid-propanol system at about 40% propanol, in the trifluoroacetic acid-propanol at about 50% propanol, and in the trifluoroacetic acid-acetonitrile system at about 62% acetonitrile. For convenience, the organic solvent content of the elutant will usually be increased rapidly to a level somewhat below the solvent concentration at which the IL-2 elutes followed by a slow gradient change in the range of about 0.1% to 1.0%/min. The most preferred solvent system is trifluoroacetic acid-acetonitrile, especially 0.1% trifluoroacetic acid-acetonitrile, because it is a higher resolution system that the acetic acid-propanol system.

As soon as the IL-2 is recovered from the chromatography step it is precipitated by neutralization with a base such as $Na_2HPO_4$ or NaOH and redissolved in a chaotropic agent as defined above, subjected to gel filtration desalting column such as a G25 Sephadex column. The chaotropic agent may be, for example, sodium laurate, guanidine hydrochloride, urea or sodium thiocyanate. Preferably it is sodium laurate or urea. Generally the redissolving takes place in the presence of a neutralizing base depending on the solvent system used for the previous chromatography step.

After desalting, the IL-2 is collected and combined with an effective amount of sodium laurate to dissolve the IL-2. The exact amount of sodium laurate employed will depend mainly on the ultimate pH of the formulation, as well as the concentraton of IL-2. Generally, an effective amount at about pH 7.5 is from about 0.01% to 0.1% by weight per volume, preferably 0.03 to 0.1% by weight per volume. Below about 0.01% the sodium laurate is not effective as a solubilizing agent; above about 0.1% the IL-2 will precipitate from the solution. At a higher pH these optimum concentrations may vary.

The initial mixing of IL-2 and sodium laurate in water will take place at about pH 9-9.5. After the ingredients are mixed the pH is adjusted downward to about 7.0 to 7.8 inclusive, and the components are again mixed. The specific pH is critical because at certain pH values within the range of 7.0 to 8.0 the protein will not be soluble or the sodium laurate will precipitate or otherwise be ineffective. For example, if the pH is adjusted to below about 7.4–7.5 the sodium laurate will precipitate as lauric acid. A final pH of about 7.5 to 7.7 is therefore preferred.

The reagents used to adjust the pH upward or downward are not critical. Thus, any base, preferably an inorganic base such as dibasic sodium phosphate ($Na_2HPO_4$), sodium hydroxide, or ammonium hydroxide, may be used to adjust the pH to 9–9.5, and any acid, such as HCl, maleic acid, lactic acid, tartaric acid or citric acid, may be used to adjust the pH downward. The acid is preferably used in concentrated form so that the amount used will not effectively dilute the mixture so as to precipitate the IL-2.

For parenteral administration the IL-2 will be formulated in a unit dosage injectable solution form in association with a pharmaceutically acceptable parenteral vehicle. Such vehicles are inherently nontoxic and non-therapeutic. Examples of such vehicles are water, saline, Ringer's solution, dextrose solution, and 5% human serum albumin in water. Nonaqueous vehicles such as fixed oils and ethyl oleate may also be used. Liposomes may be used as carriers. The vehicle may contain minor amounts of additives such as bulking substances or toxicity modifiers such as glycerine, lactose, mannitol or dextrose, oleaginous vehicles such as benzyl benzoate, lubricants, suspending agents, chelating agents, stabilizers, or substances that enhance isotonicity and chemical stability, e.g., buffers such as tartaric acid, antimicrobial perservatives such as phenol, and antioxidants such as acentone sodium bisulfite. The IL-2 will typically be formulated in such vehicles at concentrations of about 0.1 mg/ml to 10 mg/ml, preferably 0.2 to 5 mg/ml. A preferred additive for the IL-2 formulation is mannitol, in a concentration of 2.5 to 5.0% by weight of the formulation.

After the formulation has been adjusted to a pH of 7.0 to 8.0, the formulation is preferably filtered to obtain a clear solution if the pH is adjusted to less than 8.0 as opposed to exactly 8.0, lyophilized, and finally resuspended in a neutral aqueous buffer containing the reducing agent (if necessary to keep the IL-2 in a reduced state) and the sodium laurate (to keep it in solution). The IL-2 is stable in this form and may be stored for further treatment and formulation before being used.

FIG. 1 illustrates the details of the individual process steps of the present invention including the culture of the transformed microorganisms in an appropriate fermentation medium through the final step where the purified IL-2 is lyophilized for reconstitution into therapeutic formulations. In this scheme a further step involves oxidation of IL-2 after it has been separated by gel filtration and purification of the oxidized product by RP-HPLC or gel filtration followed by RP-HPLC. This results in efficient removal of contaminants surviving the gel filtration as well as unwanted oxidation products. A preferred oxidation procedure is to oxidize a fully reduced microbially produced synthetic IL-2 having an amino acid sequence substantially identical to a useful IL-2, which sequence includes cysteines which in the useful IL-2 are linked intramolecularly to form a cystine in a controlled manner so that the cysteines are oxidized selectively to form the cystine. In this process the fully reduced microbially produced synthetic IL-2 is reacted with an oxidizing agent that oxidizes cysteines selectively in an aqueous medium at a pH at least about one-half pH unit below the $pK_a$ of said cysteines. The concentration of synthetic protein in this reaction mixture is less than about 5 mg/ml and the mol ratio of oxidizing agent to protein is at least stoichiometric, with the proviso that the oxidizing agent is in excess in the terminal portion of the reaction. One preferred oxidizing agent is o-iodosobenzoic acid. RP-HPLC purification of the oxidized product may be carried out under the conditions described above in the absence of a reducing agent and in the presence of a detergent at a concentration equal to or less than those used in the above described gel filtration.

The purity of the IL-2 after the chromatography step(s) is at least about 95% and usually at least about 98%. This highly pure material contains less than about 5 ng endotoxin, usually less than about 0.01 ng endotoxin per 1,000,000 International Units IL-2 activity.

The HPLC pool of oxidized IL-2 is precipitated by adding $Na_2HPO_4$. The precipitate is then collected by centrifugation and redissolved in sodium laurate and $Na_2HPO_4$. The redissolved precipitate is loaded on a gel filtration column, such as a Sephadex G-25 column, and the IL-2 is collected from the column. The IL-2 collected is virtually free of solubilizing agent and sodium laurate. This collected IL-2 is then formulated with the sodium laurate at pH 9.1 and then the pH is adjusted to 8.0 using 1M HCl.

The formulation is then lyophilized and ready for use. This process results in a formulation which is virtually free of SDS yet is in solution form.

Figure 2:
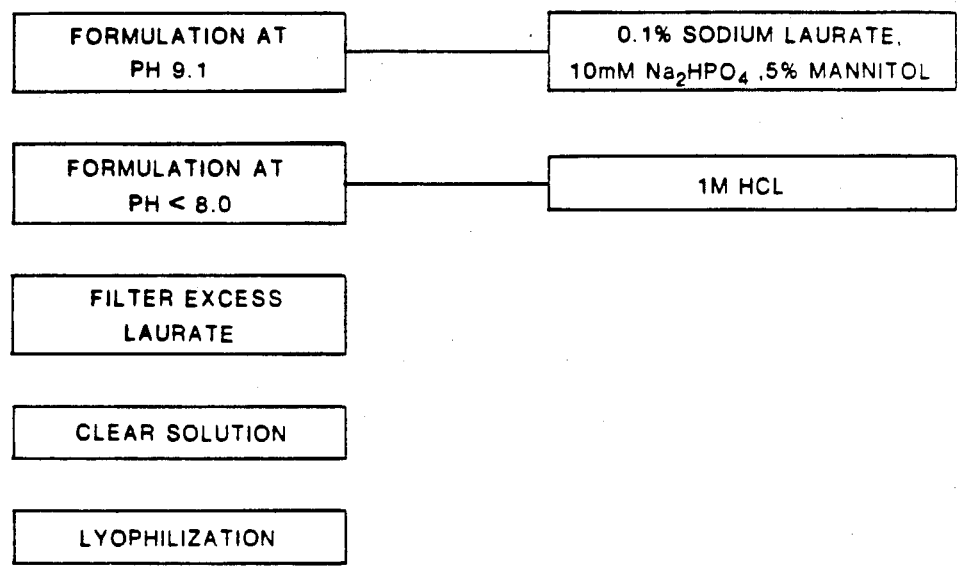
FIG. 2 shows a flow diagram as in FIG. 1 except that the formulation is adjusted to pH <8.0.

FIG. 2 illustrates the embodiment where the formulation of sodium laurate and IL-2 at pH 9.1 is adjusted to a pH less than 8.0 with 1M HCl. In this instance, the adjusted composition is preferably filtered to remove excess sodium laurate to obtain a clear solution and is then lyophilized.

The IL-2 composition herein may be used to enhance the proliferative responses of human peripheral blood mononuclear cells or murine thymocytes, to enhance the immune response in humans and in animals against bacterial, parasitic, fungal, protozoan and viral infections, and to support the growth of continuous T cell lines.

In a preferred embodiment for formulating β-HIFN, the individual process steps are summarized below:
 growing the transformed bacterial hosts in an appropriate fermentation medium;
 concentrating the bacteria in the fermentation medium by cross-flow filtration;
 mechanically homogenizing the bacteria to disrupt the cell walls of the bacteria;
 separating solid cellular material from the remainder of the homogenate by centrifugation;
 solubilizing the solid cellular material by suspending it in an aqueous solution of sodium dodecyl sulfate (SDS) at a protein to SDS ratio of about 1:3;
 extracting the β-HIFN from the aqueous phase with 2-butanol or 2-methyl-2-butanol or mixtures thereof by continuous cocurrent extraction;
 heating the 2-butanol or 2-methyl-2-butanol phase to about 60° C. for about 10 to 20 minutes; or
 aging the 2-butanol phase overnight;
 centrifuging the mixture and discarding the precipitated impurities;
 contacting the 2-butanol or 2-methyl-2-butanol phase with an aqueous buffer and adjusting the pH of the mixture to about 5.5 to precipitate the β-HIFN;
 collecting the precipitated β-HIFN by centrifugation;

solubilizing the β-HIFN with distilled water or with an aqueous solution of sodium dodecyl sulfate at a protein to SDS ratio of about 1:3;

adjusting the pH of the solution to about 9.5 and reducing the solubilized β-HIFN with dithiothreitol;

purifying the reduced β-HIFN by chromatography;

collecting the eluted fraction of the purified β-HIFN;

further purifying the β-HIFN by gel chromatography;

collecting the eluate containing the purified β-HIFN;

adding sodium laurate to the eluate;

adjusting the pH of the eluate to about 9-9.5;

mixing the formulation;

adjusting the pH of the formulation down to pH 7.0 to 8.0; and lyophilizing the β-HIFN sample, if desired.

Ten mM dithiothreitol may be optionally included in the initial solubilization step and the mixture heated to about 90° C. for about 10 minutes.

The microorganisms transformed with β-HIFN encoding genes are grown in a suitable growth medium, typically to an optical density (OD) of at least about 10 at 680 nm, and preferably between about 50 and 100 at 680 nm. The composition of the growth medium will depend upon the particular microorganism involved. The aqueous growth medium contains compounds that fulfill the nutritional requirements of the microorganism of choice. Growth media will typically contain assimilable sources of carbon and nitrogen, energy sources, magnesium, potassium and sodium ions, and optionally amino acids and purine and pyrimidine bases. (Review of Medical Microbiology, Lange Medical Publications, 14th Ed pp. 80–85 (1980)). Growth media for *E. coli* are well known in the art. Depending upon the particular solubilizing agent used in the invention process it may be desirable to minimize the amount of substances in the growth medium that may decrease the solubility of the solubilizing agent in water. For instance, potassium ions affect the solubility of SDS and, therefore, should be kept to a minimum when SDS is used as a solubilizing agent in the process, or removed by diafiltration following the concentration step.

Once the culture has reached the desired cell density, the cells are optionally killed or inactivated by heating or adding to the medium a cytotoxic agent such as chloroform or toluene that may be removed easily after the cells have been killed. The cells are thereafter optionally concentrated to about 20 to 150 mg/ml, preferably 80 to 100 mg/ml (OD 40 to 300, preferably 160 to 200 at 680 nm) by crossflow filtration, centrifugation, or other conventional methods.

Following the concentration step, the cell membranes of the microorganisms are disrupted to facilitate the solubilization of the particulate matter in the concentrate. β-HIFN assays for biological activity indicate that much of the interferon is associated with (i.e., contained in or bound to) the cell membrane. Accordingly, disruption of the cell membrane enhances the contact of the solubilizing agent with the membranes and thus increases the rate at which the interferon associated with the membrane goes into solution. Conventional cell disruption techniques such as homogenization, sonication, or pressure cyclding may be used in this step of the process. A preferred method is using a bead mill or a pressure homogenizer. Either before or after the disruption, the pH of the liquid phase of the concentrate or disruptate, as the case may be, is adjusted, if necessary, to a level that facilitates dissolution of the solubilizing agent and the particulate matter in the concentrate/disruptate. The pH may be so adjusted by adding suitable buffers or NaOH. In most instances a pH in the range of about 7 to about 8 is preferred.

After the cells have been disrupted the particulate matter can be separated from the liquid phase of the disruptate and resuspended in an aqueous medium buffered to the optimal pH for solubilization. The protein concentration of the cell suspension after solubilization is in the range of about 2 to about 15 mg/ml, preferably 6 to 8 mg/ml.

The solubilization of the particulate cellular material, including the β-IFN, can be carried out concurrently with the disruption or sequentially following the disruption. It is preferably carried out as a separate step following the disruption. The solubilization is preferably carried to completion—that is, substantially all of the particulate matter (e.g., protein, lipids, nucleic acids, phospholipids) in the disruptate is dissolved into the aqueous medium. Substantially complete dissolution of the particulate matter is achieved by adding an appropriate solubilizing agent to the aqueous suspension. Surfactants (detergents) which have a suitable hydrophobic-hydrophilic balance to solubilize β-HIFN and which form a complex with β-HIFN that can be extracted into the organic phase can be used in the invention. Strong natural or synthetic anionic surfactants such as alkali metal salts of fatty acids and alkali metal alkyl sulfates may be used. Such agents will usually contain 10 to 14 carbon atoms. Sodium dodecyl sulfate (SDS) and sodium laurate are particularly preferred solubilizing agents. Examples of other solubilizing agents that can be used in the process include but are not limited to sodium dodecyl sulfonate, sodium decyl sulfate, sodium tetradecyl sulfate, sodium tridecyl sulfonate, sodium myristate, sodium caproylate, sodium dodecyl N-sarcosinate, and sodium tetradecyl N-sarcosinate.

The amount of solubilizing agent used in the solubilization depends upon the particular agent and the amount of protein to be solubilized. In most instances, solubilizing agent to protein weight ratios in the range of about 1:1 to 10:1 are sufficient. When SDS is used, an SDS to protein ratio of about 1:1 to about 5:1, preferably about 3:1, is used. Temperatures in the range of 15° C. to 60° C. are normally used in the solubilization. Mixing may be employed to enhance contact between the solution and particulate matter and thus decrease the time it takes to dissolve the cellular matter. The solubilization is considered complete when the solution is substantially clear. ODs of about 4.0 to 8.0 at 280 nm are characteristic of the end point of the solubilization process.

Following the solubilization, the ionic strength of the solution is adjusted, if necessary, to a level at which the solution and organic extractant are substantially immiscible. The ionic strength is in the range of about 0.05 to 0.15. Inorganic salts, including NaCl and the like, are added to the solution for this purpose. Such ionic strengths enable phase separation after the extraction. The extractants used in the process are alcohols such as 2-butanol, 2-methyl-2-butanol, or mixtures thereof. The mixtures preferably contain less than about 50% by volume of 2-methyl-2-butanol. 2-Butanol is the preferred extractant. The ability of these alcohols to extract human β-IFN from the solubilizate is specific. The extractant is normally combined with the aqueous solution of β-HIFN in volume ratios in the range of about 0.8:1 to about 3:1, preferably about 1:1 (extractant:aqueous solution). The extraction can be carried out using conventional batch or continuous liquid-liquid extraction techniques and equipment. The extraction is normally carried out at about 20° C. to 100° C. and involves contact times in the range of about one minute to one hour. The optimum contact time depends upon the particular solubilizing agent and extractant combination. When SDS is used, shorter times in the above range can be used. When sodium laurate is used, longer times in the range must be used. The pH of the extraction mixture ranges between about 6 and 9, with a pH of about 7.5 being preferred when SDS is used and a pH of about 8.5 when sodium laurate is used.

Upon completion of the extraction, the aqueous phase and extractant phase are separated and the β-HIFN is isolated from the extractant phase. The particular isolation procedure used depends upon the solubilizing agent involved and the desired degree of purity of the final product. Various isolation techniques such as precipitation, molecular sieve chromatography, affinity chromatography, and electrophoresis are employed. In instances in which SDS is used, the β-HIFN together with other proteins are precipitated from the extractant by mixing the extractant solution with aqueous buffer at volume ratios of about 2:1 to about 5:1, preferably about 3:1, and reducing the pH, typically to the range of about 5 to 7. The recovery of β-HIFN in the pH range of 4 to 8 shows a downward trend in the recovery of the protein with increasing pH, with an appreciable loss in the recovery of greater than 60% at a pH of about 8. Separation of the precipitate from the supernatant and evaporation of residual extractant from the precipitate provide a product that is greter than about 90% pure protein provided that the pH of the precipitation step is greater than 5.5. This product also contains minor amounts of nucleic acids ($\geq 1\%$ to 2% by weight) and SDS (<1% w/v). After further purification by methods known in the art, including but not limited to chromatography, sodium laurate is added at a pH of about 9 to 9.5 as described above for IL-2, and then the pH is adjusted to about 7.0 to 8.0 as described above. Prior to addition of sodium laurate the β-HIFN may be optionally reduced with appropriate reducing agents. Mercaptoethanol, glutathione, cysteine and dithiothreitol (DTT) are normally employed, DTT being the most preferred.

The β-HIFN thus isolated can be lyophilzed or stored in solution pending use. Nontoxic, nontherapeutic, nonimmunogenic stabilizers may be optionally added to the β-HIFN. Diluents that can be used in the solutions for therapeutic or clinical administrations are selected from aqueous based vehicles commonly used to formulate pharmaceuticals for animal or human administration. The diluent should, of course, not affect the biological activity of the β-HIFN. Examples of such diluents include distilled water, physiological saline, Ringer's solution, dextrose solution, and Hank's solution. The same diluents can be used to reconstitute lyophilized β-HIFN.

The β-HIFN formulation may be used for anti-viral, anti-cancer, immunoregulatory and other therapeutic purposes.

When used in vivo for therapy, the protein formulation is administered to the patient in therapeutically effective amounts (i.e., amounts that eliminate or reduce the patient's diseased condition). They will normally be administered parenterally, preferably intravenously. The dose and dosage regimen will depend upon the nature of the disease being treated and its population, the characteristics of the particular formulation, e.g., its protein concentration, the patient, and the patient's history. The amount of formulation administered will typically be in the range of about 0.1 to about 10 mg/kg of patient weight.

The invention process is further described by the following examples. These examples are not intended to limit the invention in any manner. In the examples all parts and percentages are given by weight per volume and all temperatures are given bgy degrees Centigrade unless otherwise noted.

EXAMPLE 1

A mutein IL-2 designated des-Ala Ser$_{125}$ IL-2 was recovered from *E. coli*. The amino acid sequence of this IL-2 is different from that of the native molecule in that the cysteine at position 125 has been changed to serine and the initial N-terminal alanine residue is missing. The strain of des-Ala Ser$_{125}$ IL-2-producing *E. coli* used in this example was deposited at the American Type Culture Collection on Mar. 6, 1984 under accession number 39,626.

The *E. coli* thus transformed were grown in a fermenter using the following growth medium.

| | |
|---|---|
| $(NH_4)_2SO_4$ | 150 mM |
| $KH_2PO_4$ | 21.6 mM |
| $Na_3$ Citrate | 1.5 mM |
| $ZnSO_4.7H_2O$ | 30 mM |
| $MnSO_4.H_2O$ | 30 mM |
| $CuSO_4.5H_2O$ | 1 mM |
| pH adjusted to 6.50 with 2.5 N NaOH | |
| autoclaved | |
| Sterile Additions (post autoclave) | |
| $MgSO_4.7H_2O$ | 3 mM |
| $FeSO_4$ | 100 μM |
| L-tryptophan | 14 mg/l |
| Thiamine-HCl | 20 mg/l |
| Glucose | 5 g/l |
| Tetracycline | 5 mg/l |
| Ethanol (optional) | 2% |
| Casamino acids | 2% |

Dow Corning Antifoam B, 20% solution, glucose, 50% solution, and KOH, 5N, were added on demand.

The pH of the fermenter was maintained at 6.8 with 5N KOH. Resdiual glucose was maintained between 5 and 10 g/l, dissolved oxygen at 40%, and temperature at 37 ±1° C. The casamino acids (20% stock solution) were added when the OD$_{680}$ was about 10. Harvest was made 3 hours after the OD$_{680}$ reached about 20.

The harvested material was concentrated by hollow fiber filtration and/or centrifugation. Twenty to forty g (wet weight) of the concentrate were resuspended in 200 ml of 50 mM Tris, 1 mM ethylenediaminetetraacetic acid (EDTA) (pH 8.1–8.5) (Tris/EDTA buffer). The suspension was centrifuged at 3,000–4,000×g for 10 minutes, the supernatant was removed, and the solids were resuspended in 200 ml Tris/EDTA buffer at 4° C. The suspension was loaded into a sonicator (Heat Systems, Model W-375) and sonicated at 4° C. for 45 minutes (end point=OD$_{680}$ reduction of about 85%) using large probe, pulsing with 50% duty on power setting "9". An alternative disruption technique is to pass the suspension three times through a Manton-Gaulin homogenizer. Cellular debris was separated from the disruptate by centrifuging at 4,500×g for 10 minutes.

The cellular debris was suspended in 50 mM Tris, 1 mM EDTA pH 8.5 buffer at room temperature at a ratio of about 1:4.5 (w/v). DTT was added to a final concentration of 25 mM. 8M urea (Schwartz/Mann ultrapure) in the same Tris/EDTA buffer was slowly added to the suspension over 5 minutes with rapid stirring (final urea concentration, 4M). After continued slow stirring at room temperature for 30 minutes, the suspension was centrifuged at 12,000×g for 15 minutes to recover extracted cellular debris. (If a solid phase does not form, the supernatant is withdrawn, an equal volume of Tris/EDTA buffer is added and the mixture is centrifuged.)

The extracted cellular debris was then resuspended in 9 ml of 50 mM sodium phosphate, 1 mM EDTA at pH 7.0. The suspension was then solubilized by adding solid SDS to the suspension to a final concentration of 5% w/v.

The 5% SDS solution was diluted to 2% SDS with 0.1M $Na_2PO_4$, pH 8.0. The protein concentration was determined, the pH was adjusted to 8.5, and DTT to 50 mM and EDTA to 2 mM were added. The mixture was heated to 40° C. under $N_2$ to reduce the IL-2. The mixture was then cooled and the pH was adjusted to 5.0.

The solution was then extracted at a 1:1 ratio (v/v) with 2-butanol containing 1 mM DTT at room temperature. Residence time was 2–2.5 minutes. The extraction was carried out in a liquid-liquid phase separator using a flow rate of 200 ml/min. The organic extract was separated and its pH was adjusted to 8.0 with NaOH. The extract was then added slowly to 0.1% SDS in 10 mM $Na_2PO_4$, 2 mM DTT, pH 6 and stirred for 15–20 minutes. The resulting precipitate was separated and the resulting paste was resuspended in 5% SDS in PBS.

The solution was clarified by centrifugation and then 200 ml of the clarified solution was reduced using 10 mM DTT in the presence of 2.5 mM EDTA at pH 8.0 and 60° C. for 30 minutes. The suspension was centrifuged at 45K for 2 hours. The supernatant (35 ml) was loaded on a S-200 (K-50, Pharmacia) column and eluted with acetate pH 5.5 (50 mM), DTT (2 mM), EDTA (1 mM) and SDS (0.1%) at a rate of 1.5 ml/min. The S-200 pool (270 ml, $A_{280}$=1.77) was about 33% pure as determined by HPLC.

A portion of the S-200 pool (35 ml) was acidified with trifluoroacetic acid (TFA) to pH 2.0, and then loaded at 2.5 ml/min. on a semi-preparative (1.3 cm) C-4 Vydac column that was freshly prepared. This was done three times with 35 ml each loading. The solvent used for this semi-preparative purification was acetonitrile (0.1% TFA, buffer B) and the gradient that was used was 0% to 45% buffer B in 15 minutes folloawed by 45% to 75% of B in 200 minutes. The IL-2 pool came out as 76 ml (three runs) with an $A_{280}$=0.326 that corresponds to about 25 mg of IL-2 and which is about 15% yield. This HPLC run was diluted into 1600 ml of $Na_2PO_4$ buffer (0.1M, pH 7.0, 0.1% SDS) and then concentrated to 50 ml by using an Amicon cell equipped with a 76 mm PM-10 membrane. The concentrate was washed with three volumes of 50 ml each of $Na_2PO_4$ (50 mM) pH 7 buffer which contained 0.1% SDS. The final volume was 43 ml with an $A_{280}$=0.65.

Before the oxidation was carried out, the total thiol content of the protein solution was determined with 2,2'-dithiodipyridine. This determination was necessary in order to calculate the minimum theoretical amount of o-iodosobenzoic acid that had to be added to the IL-2 solution to achieve complete oxidation. o-Iodosobenzoic acid solution (1 mM, 50 ml) was prepared by dissolving the compound (13.4 mg) in about 45 ml of $H_2O$ by sonicating the mixture for a few minutes and then by stirring and slowly adding NaOH (1N) to dissolve the acid. The alkaline solution was added to obtain a final pH of 8.0 to 8.5. The volume of the oxidant solution was adjusted to a final volume of 50 ml. A sulfhydryl group determination was done in order to determine the total amount of oxidant needed for a complete oxidation. This corresponded to the total thiol concentration divided by two plus a 15 micromolar excess of the oxidant. The controlled oxidation was performed by adding the o-iodosobenzoic acid solution at a flow rate of 0.5 ml/hour to the IL-2 solution (50 mM $Na_2PO_4$, pH 7 or 7.5). The degree of the oxidation was monitored by reverse phase HPLC. The oxidation was stopped by lowering the pH of the solution to 5.5 using concentrated acetic acid. HPLC analysis of the oxidized product showed that it comprised about 80% of the desired oxidized IL-2, about 13% undesired isomers (the isomers were collected, assayed for IL-2 activity and found to be inactive) and about 6% reduced (unoxidized) IL-2.

The oxidized product was separated from iodosobenzoate and iodobenzoate by G-25 column chromatography using 0.1% SDS, 50 mM sodium acetate, 1 mM EDTA, pH 5.5. The IL-2 was then separated from the solution by RP-HPLC as follows. The solution was diluted 10-fold in 0.1% trifluoroacetic acid (TFA) and was applied to a 4.6 mm I.D.×5 cm L. Brownlee Aquapore RP-300 column equilibrated in 0.1% TFA. The IL-2 was eluted with a gradient of 30–60% acetonitrile containing 0.1% TFA over 45 minutes. The resulting purified recombinant IL-2 product had an IL-2 content greater than about 95% as determined by reducing SDS-PAGE analysis and an endotoxin content of less than about 0.1 nanograms/mg of IL-2, and it was substantially free of pyrogens as determined by the U.S. P. raabbit pyrogen test at a dosage of $3.3 \times 10^5$ U/kg.

The process up to this point is shown in FIG. 1. A variation of this process may be used to produce IL-2 on a larger scale. Thus, there may be (1) minor changes in the buffers, (2) use of an acetic acid-propanol solvent system in the RP-HPLC, and (3) the inclusion of post-oxidation dilution/diafiltration, S-200 gel filtration, and ultrafiltration steps. The process up to HPLC as shown in FIG. 1 may be modified with various refinements, for example, following the second S-200 column pass, in 1% SDS, the IL-2 solution may be diluted 1:10 to give a 0.1% SDS concentration and then diafiltered against 10 mM phosphate buffer at a pH of 7.5 and 5 ppm SDS. The solution may be then concentrated as required for appropriate use dosage.

A total of 100 ml of the HPLC pool described above containing 250 mg oxidized, purified IL-2 in 0.1% trifluoroacetic acid and 60% acetonitrile was precipitated by adding 6 ml of 0.5M $Na_2HPO_4$ to the pool. The precipitate was then collected by centrifuging at 5,000×g for 15 minutes. The solid centrifugate was then redissolved in 120 ml of 0.5% sodium laurate and 10 mM $Na_2HPO_4$. This solution was loaded on a Sephadex G-25 column, 5×80 cm using a column buffer of 10 mM $Na_2HPO_4$, pH 9.1 and a flow rate of 20 ml/min. The IL-2 was then collected from the column in a pool of 150 ml containing 1.5 mg IL-2 per ml. The concentration of sodium laurate in this pool was less than or equal to 0.01% and the SDS concentration, as determined by the acridine orange assay method for SDS described by *Anal Bio-* chem, Vol. 118, p. 138–141 (1981), was less than or equal to 0.4 μg/mg IL-2.

The IL-2 collected from the column was combined with water, sodium laurate, $Na_2HPO_4$ and mannitol to a pH of 9.1 to yield final concentrations of:

| IL-2 | 0.25 mg/ml |
|---|---|
| Sodium laurate | 0.07% |
| $Na_2HPO_4$ | 10 mM |
| Mannitol | 5% |

The final concentration of SDS as determined by the acridine orange assay described above was less than or equal to 0.4 μg/mg IL-2 or 0.1 μg/ml.

The formulation at pH 9.1 was adjusted to pH 7.5 by adding 1M HCl thereto. It was then lyophilized by known techniques.

The lyophilized formulation was virtually free of SDS, yet the IL-2 was still soluble in the formulation.

EXAMPLE 2

This example illustrates the effect of final pH on solubility of the IL-2. The procedure of Example 1 was followed except that the formulation at pH 9.1 had final concentrations of:

| IL-2 | 0.25 mg/ml |
|---|---|
| Sodium laurate | 0.03% |
| $Na_2HPO_4$ | 10 mM |
| Mannitol | 2.5% |

The final concentration of IL-2 was 0.64 mg/ml. This formulation was split into two portions, one which was adjusted to pH 7.5 with 1N HCl to yield a clear (IL-2 soluble) solution and one adjusted to pH 7.0 to yield a solution which is slightly hazy, indicating some IL-2 insolubility. The formulaton when adjusted to pH 6.5 became hazier and was very hazy after 1 minute. When sodium hydroxide was added to the formulation to a pH of 7.5, the solution became almost completely clear.

EXAMPLE 3

This example illustrates the effect of sodium laurate concentration on IL-2 solubility. The procedure of Example 2 was followed except that 5% mannitol was employed rather than 2.5% and no sodium laurate was added to the formulation before adjustment to pH 7.5. The amounts of ingredients were:

| 9.75 ml of the IL-2 pool |
|---|
| 0.5 ml 0.5 M $Na_2HPO_4$ |
| 5.0 ml 25% mannitol |
| 11.0 ml $H_2O$ |

The formulation after adjustment to pH 7.5 turned hazy, indicating that the IL-2 was not soluble therein.

A formulation containing 0.01% sodium laurate was prepared using the following concentrations of ingredients:

| 9.75 ml of the IL-2 pool |
|---|
| 0.5 ml 0.5 M $Na_2HPO_4$ |
| 2.5 ml mannitol (25%) |
| 0.25 ml 1% sodium laurate |
| 10 ml $H_2O$ |

The formulation after adjustment to pH 7.5 was clear, indicating that the IL-2 was soluble in the mixture.

A formulation containing 0.1% sodium laurate was prepared using the following concentrations of ingredients:

| 9.75 ml of the IL-2 pool |
|---|
| 0.5 ml 0.5 M $Na_2HPO_4$ |
| 2.5 ml mannitol (25%) |
| 2.5 ml 1% sodium laurate |
| 10 ml $H_2O$ |

The formulation after adjustment to pH 7.5 was clear, indicating that the IL-2 was soluble in the mixture.

A formulation comprising 0.06% sodium laurate was prepared using the following concentrations of ingredients:

| 9.75 ml of the IL-2 of this example |
|---|
| 0.5 ml $Na_2HPO_4$ |
| 2.5 ml 25% mannitol |
| 1.5 ml 1% sodium laurate |
| 8 ml $H_2O$ |

When the pH of this formulation was adjusted to 7.5 with 1N HCl the solution remained clear.

A control formulation containing 1% SDS rather than sodium laurate at pH 7 was prepared using the following concentrations of ingredients:

| 9.75 ml of the IL-2 pool |
|---|
| 2.5 ml 10% SDS |
| 0.5 ml 0.5 M $Na_2HPO_4$, pH 7 |
| 2.5 ml 25% mannitol |
| 9.75 ml $H_2O$ |

The formulation was found to be clear.

Ultraviolet scans were performed on the formulations with 0%, 0.01%, 0.03% and 0.1% sodium laurate and with 1% SDS. These scans indicated that the 0.1% laurate formulation has the same stability as the 1% SDS formulation.

A control formulation containing 0.1% sodium octanoate was prepared using the following concentrations of ingredients:

| 9.75 ml of the IL-2 pool |
|---|
| 0.5 ml 0.5 M $Na_2HPO_4$ |
| 2.5 ml 25% mannitol |
| 0.25 ml 1% sodium octanoate |
| 10 ml $H_2O$ |

When the formulation was adjusted to pH 7.5 it appeared slightly hazy. When the sodium octanoate was added to a level of 0.2%, the formulation was still hazy. Therefore, sodium octanoate (a $C_8$ fatty acid salt) is not effective as a stabilizer as is sodium laurate (a $C_{12}$ fatty acid salt).

When the above experiment was repeated using sodium tetradecanoate (a $C_{14}$ fatty acid sodium salt), the salt would not remain in solution. When the above experiment was repeated using sodium decanoate (a $C_{10}$ fatty acid salt), the formulation was hazy. Only the $C_{12}$ fatty acid salt was effective among these fatty acids tested.

EXAMPLE 4

The solvents for RP-HPLC were 6% acetic acid/water and 6% acetic acid/2-propanol in the procedure of Example 1. The IL-2 elutes at about 40% 2-propanol during gradient elution. The HPLC pool was diluted with one volume of 0.8N sodium hydroxide. The IL-2 precipitated and was collected by centrifugation. The precipitated IL-2 was then redissolved in sodium laurate and $Na_2HPO_4$ and formulated as described in Example 1.

It is expected that parenteral injection of the formulations containing the recombinant IL-2 or ω-HIFN protein and sodium laurate in effective amounts into patients requiring treatment with the protein will be effective because the protein is soluble at physiological pH and the exposure of the protein to strongly alkaline pH is eliminated.

The present invention is seen to provide a pharmaceutical composition suitable for parenteral injection into patients which contains recombinant IL-2 or β-HIFN and an effective amount of sodium laurate. The sodium laurate not only has the properties necessary to stabilize the protein but also can be readily metabolized once in the blood so that it would not be, for example, concentrated in the liver. Total fatty acids, including sodium laurate (sodium dodecanoate), are present in the blood at levels of 2-4 mg/ml or about 12 to 30 g total fatty acids in the whole blood system. The injected sodium laurate will bind quickly to serum albumin and enter the metabolic cycle of the bulk fatty acids, with no problem of hemolysis or sequestration of the sodium laurate.

In addition, the process herein represents a method of formulating IL-2 or IFN-β protein containing less than 0.4 μg/ml of SDS, as opposed to current levels of about 5-10 μg/ml of SDS in IFN formulations and about 150 μg/ml of SDS in IL-2 formulations. In addition, the proteins obtained by this process are substantially free of other materials in the cell membrane disruptate. The process herein results in recovery of the proteins in relatively highly pure form with trace or no amounts of SDS, which proteins can be reconstituted into tbherapeutically acceptable formulations.

Modification of the above described modes for carrying out the invention that are obvious to those of skill in the fields of biochemistry, biochemical engineering, and related arts are intended to be within the scope of the following claims.

What is claimed is:

1. A stable pharmaceutical composition of matter suitable for parenteral injection into animals or humans comprising a therapeutically effective amount of a recombinant interleukin-2 protein which contains less than 4 μg sodium dodecyl sulfate per mg protein dissolved in an inert carrier medium comprising sodium laurate at a pH of about 7.0 to 8.0.

2. The composition of claim 1 wherein said protein is a mutein in which a cysteine residue not esential to biological activity has been deleted or replaced with another amino acid.

3. The composition of claim 2 wherein said protein is des-Ala-Ser$_{125}$ IL-2.

4. The composition of claim 1 wherein the pH is 7.5 to 7.7.

5. The composition of claim 1 wherein said medium is aqueous.

6. The composition of claim 1 comprising less than 0.4 μg of sodium dodecyl sulfate per mg protein.

7. The composition of claim 1 wherein the sodium laurate is present in a concentration of between 0.01 and 0.1% by weight per volume, depending on the pH of the solution.

8. The composition of claim 1 further comprising mannitol.

9. The composition of claim 3 wherein the interleukin-2 is present at a concentration of 0.25 mg/ml, the sodium laurate is present at a concentration of 0.03-0.1% by weight per volume, and mannitol is present at a concentration of 2.4-5% by weight per volume.

10. In a process for treating animals or humans with a biologically active interleukin-2 protein, the improvement which comprises parenterally injecting into the animals or humans therapeutically effective amounts of the composition of claim 1.

* * * * *